(12) United States Patent
Morita

(10) Patent No.: US 7,648,766 B2
(45) Date of Patent: Jan. 19, 2010

(54) COMPOSITE SILICONE RUBBER POWDER COATED WITH INORGANIC MICROFINES AND AN ORGANIC SILICON COMPOUND, METHOD OF ITS MANUFACTURE, AND USE THEREOF

(75) Inventor: Yoshitsugu Morita, Chiba (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 392 days.

(21) Appl. No.: 11/813,323

(22) PCT Filed: Dec. 15, 2005

(86) PCT No.: PCT/JP2005/023444

§ 371 (c)(1),
(2), (4) Date: Jul. 3, 2007

(87) PCT Pub. No.: WO2006/073055

PCT Pub. Date: Jul. 13, 2006

(65) Prior Publication Data

US 2008/0138621 A1 Jun. 12, 2008

(30) Foreign Application Priority Data

Jan. 5, 2005 (JP) ............................. 2005-001014

(51) Int. Cl.
*B32B 5/16* (2006.01)
(52) U.S. Cl. ....................... 428/403; 428/404; 428/405; 428/447; 428/448; 524/430; 524/492
(58) Field of Classification Search ................. 428/403, 428/447, 448, 404, 405; 524/430, 492
See application file for complete search history.

(56) References Cited

U.S. PATENT DOCUMENTS

| | | | | |
|---|---|---|---|---|
| 4,880,882 | A * | 11/1989 | Morita et al. ................ | 525/446 |
| 5,082,891 | A * | 1/1992 | Morita et al. ................ | 524/481 |
| 5,492,945 | A * | 2/1996 | Morita et al. ................ | 523/212 |
| 5,645,941 | A | 7/1997 | Meguriya et al. | |
| 5,756,568 | A * | 5/1998 | Morita et al. ................ | 524/268 |
| 5,908,951 | A * | 6/1999 | Kobayashi et al. .......... | 556/479 |
| 5,945,491 | A * | 8/1999 | Matyjaszewski et al. .... | 526/111 |
| 5,948,469 | A | 9/1999 | Morita et al. | |
| 6,306,957 | B1 | 10/2001 | Nakano et al. | |
| 6,380,301 | B1 | 4/2002 | Enami et al. | |
| 6,844,393 | B2 | 1/2005 | Goto et al. | |
| 7,399,803 | B2 * | 7/2008 | Morita et al. ................ | 524/430 |
| 2002/0028335 | A1 | 3/2002 | Fujiki et al. | |

FOREIGN PATENT DOCUMENTS

| | | |
|---|---|---|
| EP | 0548969 A1 | 6/1993 |
| EP | 0564253 A1 | 10/1993 |
| EP | 0661334 A1 | 7/1995 |
| EP | 0958805 A2 | 11/1999 |
| EP | 1403326 A1 | 3/2004 |
| GB | 2279616 A | 1/1995 |
| JP | 4348143 | 12/1992 |
| JP | 06-220778 | 8/1994 |
| JP | 06-298897 | 10/1994 |
| JP | 06-298940 | 10/1994 |
| JP | 7102075 | 4/1995 |
| JP | 8073592 | 3/1996 |
| JP | 9012724 | 1/1997 |
| JP | 11-222559 | 8/1999 |
| JP | 11-323086 | 11/1999 |
| JP | 2000-256558 | 9/2000 |
| JP | 2001-139815 | 5/2001 |
| JP | 2003-213133 | 7/2003 |
| JP | 2003-253122 | 9/2003 |
| WO | WO 02/097393 A3 | 12/2002 |
| WO | WO 03/072656 A1 | 9/2003 |
| WO | WO 2004/061002 A1 | 7/2004 |

OTHER PUBLICATIONS

English language translation and abstract for JP06-220778 extracted from *Searching PAJ* database dated Feb. 18, 2008, 20 pages.
English language translations and abstract for JP 06-298897 extracted from *Searching PAJ* database dated Feb. 18, 2008, pp. 50.
English language translations and abstract for JP 06-298940 extracted from *Searching PAJ* database dated Feb. 18, 2008, pp. 45.
English language translations and abstract for JP 11-222559 extracted from *Searching PAJ* database dated Feb. 18, 2008, pp. 38.
English language translation and abstract for JP11-323086 extracted from *Searching PAJ* database dated Feb. 18, 2008, 36 pages.
English language translation and abstract for JP08-073592 extracted from *Searching PAJ* database dated Jun. 13, 2008, 20 pages.
English language translation and abstract for JP 09-012724 extracted from *Searching PAJ* database dated Jun. 13, 2008, 34 pages.

(Continued)

*Primary Examiner*—H. (Holly) T Le
(74) *Attorney, Agent, or Firm*—Howard & Howard Attorneys PLLC

(57) ABSTRACT

A composite silicone rubber powder comprising: (A) a silicone rubber powder having an average particle size within the range of 0.1 to 500 μm and hardness of at least 15 by type A durometer according to JIS K 6253, wherein the surface of said silicone rubber powder is coated with (B) a microfine inorganic powder having the BET specific surface area of at least 10 m²/g, said composite silicone rubber powder being characterized by the fact that the surface thereof is treated with (C) an organic silicon compound having a silicon-bonded hydrolyzable group, or with a product of partial hydrolysis of said compound, is characterized by excellent dispersibility in coating and cosmetic materials and having the possibility of improving matting properties of coating materials, and feel of use of cosmetic materials.

20 Claims, No Drawings

OTHER PUBLICATIONS

English language abstract for JP 4348143 extracted from espacenet.com database dated Feb. 18, 2008.

English language abstract for JP 7102075 extracted from espacenet.com database dated Feb. 18, 2008.

English language abstract for JP 2000-256558 extracted from espacenet.com database dated Oct. 25, 2007.

English language abstract for JP 2001-139815 extracted from espacenet.com database dated Oct. 25, 2007.

English language abstract for JP 2003-213133 extracted from espacenet.com database dated Oct. 25, 2007.

English language abstract for JP 2003-253122 extracted from espacenet.com database dated Feb. 18, 2008.

PCT International Search Report for PCT/JP2005/011864, Jan. 20, 2006, 5 pages.

PCT International Search Report for PCT/JP2005/018405, Mar. 22, 2006, 6 pages.

PCT International Search Report for PCT/JP2005/023195, Feb. 17, 2006, 3 pages.

PCT International Search Report for PCT/JP2005/023445, Apr. 19, 2006, 3 pages.

Yongxin Han et al. "Silicon Directed *ipso*-Substitution of Polymer Bound Arylsilanes: Preparation of Biaryls via", Tetrahedron Letters, vol. 37, No. 16. 1996, pp. 2703-2706.

Schultz et al., "The Synthesis Of Trimethylsilylmethoxymethyl Chloride", OPPI Briefs, vol. 27, No. 5, 1995, pp. 572-574.

Hojo et al., "New Access To Carbonyl Ylides By The Silicon-Based 1,3- Elimination and Their . . .", Tetrahedron Letters, vol. 34, No. 37, 1993, pp. 5943-5946.

Boons et al., "Use of (Phenyldimethylsilyl)methoxymethyl and (Phenyldimethylsilyl)methyl ethers . . .", Tetrahedron Letters, vol. 31, No. 15, 1990, pp. 2197-2200.

Hasseberg et al., "104. Synthese von Orellin", Helvetica Chimica Acta—vol, 71, No. 5, 1988, pp. 957-963.

Guedin-Vuong et al., "An Easy Access To Homopropargylic Ethers", Bulletin De La Societe Chimique De France, No. 2, 1986, pp. 245-252.

Pyne et al., "Chiral and Stereochemical Control via Intramolecular Diels-Alder Reaction of Z Dienes", J. American Chemical Society, vol. 104, No. 21, 1982, pp. 5719-5728.

Lipshutz et al., "B-(Trimethylylsily1) Ethoxymethyl Chloride . . . ,"Tetrahedron Letters, vol. 21, No. 35, 1980, pp. 3343-3346.

Shikhiev et al., "Synthesis and Reactions of Unsaturated Organosilicon Compounds", J. Of General Chemistry of the USSR, vol. 41, No. 3, 1971, pp. 617-619.

Shipov et al., "Synthesis of Alkyl Chloromethyl Ethers", J. Of General Chemistry of the USSR, vol. 59, No. 5.2, 1989, p. 1067.

Miramon et al., "Short Synthesis of Polyoxygenated Macrocyclic . . .", Journal of Organic Chemistry, vol. 69, No. 20, 2004, pp. 6949-6952.

Shikhiev et al., "Synthesis and Reactions of Some Heteroorganic Ethers . . .", J. Of General Chemistry of the USSR, vol. 45, No. 1, 1975, pp. 91-93.

\* cited by examiner

US 7,648,766 B2

COMPOSITE SILICONE RUBBER POWDER COATED WITH INORGANIC MICROFINES AND AN ORGANIC SILICON COMPOUND, METHOD OF ITS MANUFACTURE, AND USE THEREOF

RELATED APPLICATIONS

This application claims priority to and all the advantages of International Patent Application No. PCT/JP2005/023444, filed on Dec. 15, 2005, which claims priority to Japanese Patent Application No. JP2005-001014, filed on Jan. 5, 2005.

TECHNICAL FIELD

The present invention relates to a composite silicone rubber powder comprised a silicone rubber powder, the surface of which is coated with a microfine inorganic powder. The invention also relates to a method of manufacturing the aforementioned composite silicone rubber powder, as well as to a coating material and a cosmetic material comprised the aforementioned composite silicone rubber powder. More specifically, the invention relates to a composite silicone rubber powder that is characterized by excellent dispersibility in coating and cosmetic materials and imparts improved matting properties to coating materials and comfortable feeling of use to cosmetic materials. Furthermore, the invention relates to an efficient method of manufacturing the aforementioned composite silicone rubber powder, as well as to coating materials capable of forming coating films with improved matting properties and to cosmetic materials characterized by comfortable feeling of use.

BACKGROUND ART

It is known that dispersibility of a silicone rubber powder in coating materials, cosmetic materials, ink, thermosetting organic resins, thermoplastic organic resins, etc., can be improved by using a composite silicone rubber powder obtained by coating the surface of a conventional silicone rubber powder with a microfine inorganic powder. For example, Japanese Unexamined Patent Application Publication No. (hereinafter referred to as "Kokai") H4-348143 discloses a composite silicone rubber powder obtained by coating the surface of a silicone rubber powder having an average particle size of 0.1 to 200 μm with a microfine metal oxide powder. Also Kokai H7-102075 discloses a composite silicone rubber powder composed of a silicone rubber powder having an average particle size of 0.1 to 200 μm and having density of silanol groups on the surface of no less than 2 per 100 Å$^2$, the surface of the silicone rubber powder being coated with a microfine powder of amorphous silica having an average particle size not exceeding 1 μm. The aforementioned composite powders are obtained by mixing an aqueous dispersion of a silicone rubber powder with a metal oxide sol and then removing water from the obtained mixture (see Kokai H4-348143) or by adding a microfine powder of amorphous silica to an aqueous dispersion of a silicone rubber powder and then heating the product in order to remove water (see Kokai H7-102075).

Even though the composite silicone rubber powders could be readily obtained, they still demonstrate insufficient dispersibility in coating and cosmetic materials. It is also impossible to sufficiently improve matting properties in coating materials and to ensure comfortable feeling of use of cosmetic materials.

It is an object of the present invention to provide a composite silicone rubber powder characterized by excellent dispersibility in coating and cosmetic materials and having the possibility of improving matting properties of coating materials and feeling of use of cosmetic materials. It is another object to provide an efficient method of manufacturing the aforementioned composite silicone rubber powder. It is still another object to provide coating materials capable of forming coating films with excellent matting characteristics and cosmetic materials with improved feeling of use.

DISCLOSURE OF INVENTION

A composite silicone rubber powder of the invention comprises (A) a silicone rubber powder having an average particle size within the range of 0.1 to 500 μm and hardness of at least 15 by type A durometer according to JIS K 6253, wherein the surface of the silicone rubber powder is coated with (B) a microfine inorganic powder having the BET specific surface area of at least 10 m$^2$/g, the composite silicone rubber powder being characterized by the fact that the surface thereof is treated with (C) an organic silicon compound having a silicon-bonded hydrolyzable group, or with a product of partial hydrolysis of the compound.

A method of the invention for manufacturing the composite silicone rubber powder comprises the steps of: mixing (A) a silicone rubber powder having an average particle size within the range of 0.1 to 500 μm and hardness of at least 15 by type A durometer according to JIS K 6253 with (B) a microfine inorganic powder having the BET specific surface area of at least 10 m$^2$/g; and further mixing the obtained mixture with (C) an organic silicon compound having a silicon-bonded hydrolyzable group, or with a product of partial hydrolysis of this compound.

A coating material and a cosmetic material of the invention are characterized by containing the aforementioned composite silicone rubber powder.

EFFECTS OF INVENTION

The composite silicone rubber powder of the invention is characterized by excellent dispersibility in coating and cosmetic materials and is capable of improving matting properties of coating materials, and feeling of use of cosmetic materials. The method of the invention is characterized by efficient manufacturing of the aforementioned composite silicone rubber powder, while the coating material of the invention is capable of forming a coating film with excellent matting properties, and the cosmetic material of the invention is characterized by comfortable feeling of use.

DETAILED DESCRIPTION OF THE INVENTION

Let us first consider in more detail the composite silicone rubber powder of the invention.

The silicone rubber powder that constitutes component (A) should have an average particle size within the range of 0.1 to 500 μm, preferably 0.1 to 200 μm, more preferably 0.1 to 100 μm, and even more preferably 0.1 to 50 μm. If the average particle size of the silicone rubber powder is smaller than the lower recommended limit, it would be difficult to prepare such powder and to coat the surfaces of particles with microfine inorganic powder. If, on the other hand, the average particle size exceeds the upper recommended limit, this will lower dispersibility of the obtained composite silicone rubber powder in coating and cosmetic materials. The aforementioned average particle size can be determined by measuring the silicone rubber powder contained in an aqueous or ethanol dispersion with the use of a commercially available laser-diffraction-type particle size distribution analyzer (e.g., LA-500 type instrument produced by Horiba Seisakusho Company, Ltd.). The median size, i.e., the particle size corresponding to 50% of the cumulative distribution, was used as the average particle size. Although there are no special restrictions with regard to the shape of the particles of component (A), for better dispersibility in cosmetic and coating materials as well as for better improvement in matting properties of the coating materials and the feeling of use of cosmetic materials, it is recommended that the particles have a spherical or a substantially spherical shape. Furthermore, it is recommended that the particles of component (A) have a type A durometer hardness according to JIS K 6253 of not less than 15, preferably 15 to 90, more preferably 15 to 80, and most preferably 15 to 50. If the particles have type A durometer hardness below the lower recommended limit, this will impair flowability of the obtained composite silicone rubber powder. Furthermore, when such powder is compounded with the coating material, it would be difficult to form a coating film with improved matting properties. If, on the other hand, type A durometer hardness exceeds the upper recommended limit, it would be difficult to improve the feeling of use of cosmetic material. The type A durometer hardness can be measured by making a cured sheet-like sample from the silicone rubber composition that incorporates component (A) and then measuring the hardness of the obtained rubber sheet.

The silicone rubber composition that constitutes component (A) may be represented by the following: an addition-reaction-curable silicone rubber composition that contains at least an organopolysiloxane having at least two alkenyl groups in one molecule, an organopolysiloxane having at least two silicon-bonded hydrogen atoms in one molecule, and a platinum-type compound; a condensation-reaction-curable silicone rubber composition that contains at least an organopolysiloxane having in one molecule at least two silicon-bonded hydroxyl groups or an alkoxy group, oxime group, acetoxy group, aminoxy group, or a similar hydrolyzable group, a silane-type cross-linking agent having in one molecule at least three silicon-bonded alkoxy groups, oxime groups, acetoxy groups, aininoxy, or similar hydrolyzable groups, as well as an organic tin compound, organic titanium compound, or a similar condensation-reaction catalyst; and a silicone rubber composition curable with organic peroxide that contains at least a diorganopolysiloxane having at least one alkenyl group in one molecule and an organic peroxide. Of these, most preferable is the addition-reaction-curable silicone rubber composition or the condensation-reaction-curable silicone rubber composition.

Component (A) can be obtained by the following methods: grinding a silicone rubber obtained by curing the aforementioned silicone rubber composition; forming the particles in a spray dryer by spraying and solidifying the aforementioned silicone rubber composition; and dispersing the aforementioned silicone rubber composition in water or in an aqueous solution of a surface-active agent and then curing the composition. The last-mentioned method is most preferable for preparing the silicone rubber composition with spherical or substantially spherical particles which are most suitable for dispersing in cosmetic or coating materials. The aforementioned aqueous dispersion of the silicone rubber composition can be prepared, e.g., by mixing the components in a homogenizer, colloidal mill, or a similar stirring device or an ultrasonic mixer. In this case, prior to the preparation of an aqueous dispersion of the silicone rubber composition, it is recommended to cool and control the curability of the composition. The composition can be dried by removing water from the aqueous dispersion with the use of a vacuum dryer, a hot-air-circulation oven, or a spray dryer.

In order to stabilize the shape of the particles contained in the aqueous dispersion of the silicone rubber composition, it is recommended to add a surface-active agent. Such a surface-active agent can be exemplified by the following compounds: polyoxyalkylenealkyl ether, polyoxyalkylenealkyl phenol, polyoxyalkylenealkyl ester, polyoxyalkylenesorbitane ester, polyethyleneglycol, polypropyleneglycol, ethylene oxide adducts of diethyleneglycol trimethylnonanol, or similar nonionic surface-active agents; hexylbenzene sulfonic acid, octylbenzene sulfonic acid, decylbenzene sulfonic acid, dodecylbenzene sulfonic acid, cetylbenzene sulfonic acid, myristylbenzene sulfonic acid, sodium salts of the above, or similar anionic surface-active agents; octyltrimethyl ammonium hydroxide, dodecyltrimethyl ammonium hydroxide, hexadecyltrimethyl ammonium hydroxide, octyldimethylbenzyl ammonium hydroxide, decyldimethylbenzyl ammonium hydroxide, dioctadecyldimethyl ammonium hydroxide, coconut oil trimethyl ammonium hydroxide, or similar cationic surface-active agents. These surface-active agents can be used in combinations of two or more.

When preparing the aforementioned aqueous dispersion of a silicone rubber composition, it is recommended to add the surface-active agent in an amount of 0.1 to 20 parts by mass, preferably 0.5 to 10 parts by mass, and even more preferably 0.5 to 5 parts by mass per 100 parts by mass of the silicone rubber composition. Water should be added in an amount of 40 to 2,000 parts by mass, preferably 40 to 1,000 parts by mass per 100 parts by mass of the silicone rubber composition. If water is added in an amount less than the lower recommended range, it would be difficult to prepare a uniform aqueous dispersion of the silicone rubber composition. If, on the other hand, the amount of water exceeds the upper recommended range, this will decrease productivity of the silicone rubber powder.

In order to introduce organic functional groups into component (A), the aforementioned silicone rubber composition can be additionally combined with allylglycidyl ether, vinylcyclohexene oxide, or a similar alkenyl-containing epoxy compound; vinyltrimethoxysilane, vinyltriacetoxysilane, 3-aminopropyltrimethoxysilane, 3-aminopropyltriethoxysilane, N-(2-aminoethyl)-3-aminopropyltrimethoxysilane, 3-mercaptopropyltrimethoxysilane, 3-glycidoxypropyltrimethoxysilane, 2-(3,4-epoxycyclohexyl) ethyltrimethoxysilane, 3-methacryloxypropyltrimethoxysilane, 3- aminopropylmethyldimethoxysilane, 3-glycidoxypropylmethyldimethoxysilane, or a similar organic silicone compound.

Component (A) may also contain non-crosslinking oil. Such non-crosslinking oil may be simply present in component (A) and may naturally exude therefrom or may be the one extractable by an organic solvent. The aforementioned known non-crosslinking oil may be represented by known non-crosslinking silicone oils or non-crosslinking organic oils. The non-crosslinking silicone oil may be the one that has not participated in the curing reaction. It may have a linear-chained, partially branched linear-chained, cyclic, or branched molecular structure. The linear-chained structure is most preferable. The aforementioned known non-crosslinking oils are liquid and may have a viscosity of 1 to 100,000 mPa·s, preferably 5 to 50,000 mPa·s, and more preferably 5 to 10,000 mPa·s at 25° C. If viscosity of the oil is below the recommended lower limit, it would be difficult to impart stable water repellency to the obtained composite silicone rubber powder. On the other hand, if viscosity exceeds the recommended upper limit, it would be difficult to form the silicone rubber powder and to impregnate the powder with this oil. It is recommended to use the non-crosslinking oil that shows affinity to the silicone rubber powder and is capable of imparting to them stable water-repellant properties.

The subject non-crosslinking silicone oil is generally exemplified by dimethylpolysiloxane capped at molecular terminals with trimethylsiloxy groups. Normally, this is a nonreactive silicone oil of a polysiloxane where a part of the methyl groups of the dimethylpolysiloxane is substituted by groups other than methyl groups, e.g., by alkyl groups, phenyl groups, and 3,3,3-trifluoropropyl groups. When the silicone rubber composition for the preparation of the silicone rubber powder based on an addition-reaction cross-linking already contains the non-crosslinking silicone oil, then in addition to the oils listed above, the following oils can be used: dimethylpolysiloxane capped at both molecular terminals with silanol groups, silicone oils where a part of methyl groups contained in the dimethylpolysiloxane is substituted by groups other than methyl groups, such as alkyl groups, phenyl groups, and 3,3,3-trifluoropropyl groups. The cross-linking oils that may participate in the addition reaction are the following: dimethylpolysiloxane capped at both molecular terminals with dimethylvinylsiloxy groups that remain unreacted, a copolymer of methylvinylsiloxane and dimethylsiloxane capped at both molecular terminals with trimethylsiloxy groups, dimethylpolysiloxane capped at both molecular terminals with dimethylhydrogensiloxy groups, a copolymer of methylhydrogensiloxane and dimethylsiloxane capped at both molecular terminals with trimethylsiloxy groups, and polysiloxanes where in aforementioned polysiloxanes a part of methyl groups is substituted by groups other than methyl, such as alkyl, phenyl, and 3,3,3-trifluoropropyl groups. If a silicone oil is already present in a silicone rubber composition used for forming a silicone rubber powder based on a condensation reaction, a non-crosslinking oil may also be represented by silicone oils where a part of methyl groups is substituted by alkenyl groups. Other examples of oils than can participate in a condensation reaction include dimethylpolysiloxane capped at both molecular terminals with silanol groups that remain unreacted, as well as silicone oils where a part of methyl groups of the aforementioned dimethylpolysiloxanes is substituted by groups other than methyl groups, such as alkyl, alkenyl, phenyl, and 3,3,3-trifluoropropyl groups. There are no special restrictions with regard to the types of the above-described non-crosslinking silicone oils that may be introducing into the silicone rubber powder via impregnation.

The following are specific examples of the non-crosslinking organic oils: liquid paraffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanoline acetate, stearyl alcohol, cetostearyl alcohol, oleyl alcohol, avocado oil, almond oil, olive oil, cacao oil, jojoba oil, sesame oil, sufflower oil, soybean oil, camellia oil, squalane, persic oil, castor oil, mink oil, cotton oil, coconut oil, egg yolk oil, polypropyleneglycol monooleate, neopentylglycol-2-ethylhexanoate, or similar glycolester oils; triglyceride isostearate, palm oil fatty acid triglyceride, or similar polyalcohol ester oils; polyoxyethylene lauryl ether, polyoxypropylene acetyl ether, or similar polyoxyethylene ether oils. These organic oils can be premixed with the silicone rubber composition intended for the formation of the silicone rubber powder or can be introduced into the silicone rubber powder via impregnation.

It is recommended to use non-crosslinking oil of component (A) in an amount not exceeding 80 mass %, preferably within the range of 10 to 50 mass % of component (A). If the amount of the non-crosslinking oil of component (A) exceeds the upper recommended limit, this will impair mechanical strength of component (A) and will significantly increase exudation of the non-crosslinking oil from the obtained composite silicone rubber powder. If, on the other hand, the amount of the non-crosslinking oil is below the lower recommended limit, it will be difficult to impart sufficient hydrophilic properties to the obtained composite silicone rubber powder.

Component (A) may contain a surface-active agent that can be used in the process of preparation of this component. The surface-active agent may be the same as has been defined earlier and should be used in an amount of 0.01 to 10 mass %, preferably 0.01 to 5 mass % of component (A).

The non-crosslinking oil and the surface-active agent that have to be added to component (A) may be dispersed in 1,000 g of toluene per 100 g of component (A). The dispersion is stirred in a homodisperser for 10 min. at 1,000 rpm and then for 10 min. at 500 rpm. Following this, the dispersion is left intact for 12 hours at room temperature, then stirred again for 10 min. at 500 rpm, and filtered through a filter paper for taking a sample. A dispersion is prepared by adding 750 g of toluene to the silicone rubber powder left on the filter paper, the obtained dispersion is stirred in a homodisperser for 10 min. at 1000 rpm, passed through a filter paper for sampling, the obtained filtrate is combined with the filtrate obtained after the first filtration, and the toluene component is then removed by distillation in an evaporator at a temperature of 80° C. and pressure of 70 mmHg. The amount of the obtained oil or surface-active agent may be measured in terms of its mass. Furthermore, the presence of the oil or the surface-agent can be determined by proton NMR spectral analysis, gel permeation chromatography, infrared spectroscopy, or the like.

The microfine inorganic powder of component (B) that is applied onto the surface of component (A) restricts aggregation of component (A) particles and improves flowability and dispersibility of the obtained composite silicone rubber powder. The microfine inorganic powder should have BET specific surface no less than 10 m$^2$/g, preferably no less than 50 m$^2$/g, and even more preferably no less than 100 m$^2$/g. There are no special restrictions with regard to the average particle size of component (B), provided that it can coat the surface of component (A). For example, the average particle size of component (B) may be less than 1/10 of the average particle size of component (A). Furthermore, only a part of component (B) present in the composite silicone rubber powder may be attached to the surface of the component (A). In other words, component (B) may cover either the entire surface of component (B) or only a part of its surface, while the other part will be in a loose state.

Component (B) may be exemplified by silicon oxide, titanium oxide, aluminum oxide, zirconium oxide, antimony oxide, or a similar microfine metal oxide powder; boron nitride, aluminum nitride, or a similar microfine metal nitride powder; aluminum hydroxide, magnesium hydroxide, or a similar microfine metal hydroxide powder; calcium carbonate or a similar microfine metal carbonate powder; nickel, cobalt, iron, copper, gold, silver, or a similar microfine metal powder; as well as microfine sulfides, microfine chlorides, etc. If necessary, their surfaces can be pre-treated with organoalkoxysilane, organochlorosilane, organosilazane, or similar organic silicon compounds, to provide hydrophobicity to them. From the point of view of availability, it is advantageous to use microfine metal oxide powder and especially microfine silica powder.

The organic silicon compound or a product of its partial hydrolysis that constitutes component (C) is used for improving dispersibility of the composite silicone rubber powder of the present invention. The silicon-bonded hydrolyzable groups of the aforementioned organic silicon compound may be exemplified by methoxy, ethoxy, or similar alkoxy groups; and methylethylketoxime group or similar oxime groups; acetoxy, aminoxy, and chloro groups. Of these, most preferable are alkoxy groups. In order to improve affinity of the aforementioned organic silicon compound to the surfaces of component (B), and to some extent facilitate reaction of the this compound with these surfaces, it is recommended that such a compound contain 2-(3,4-epoxycyclohexyl) ethyl group, 3-glycidoxypropyl group, 2,3-epoxypropyl group, or a similar epoxy group; 3-aminopropyl group, N-(2-aminoethyl)-3-arninopropyl group, or a similar amino group; 3-methacryloxypropyl group, or a similar methacrylic group; chloromethyl, 3,3,3-trifluoropropyl, nanofluorobutylethyl, or a similar haloalkyl group; vinyl, aryl, butenyl, pentenyl, hexenyl, or a similar alkenyl group; or octyl, or a similar long-chain alkyl group. The aforementioned organic silicon compound may contain silicon-bonded groups other than those mentioned above, e.g., methyl, ethyl, propyl, butyl, pentyl, hexyl, heptyl, or similar alkyl groups; phenyl, tolyl, xylyl, naphthyl, or similar aryl groups; benzyl, phenethyl, or similar aralkyl groups; or other univalent hydrocarbon groups.

The following are specific examples of the aforementioned organic silicon compounds: methyltrimethoxysilane, ethyltrimethoxysilane, or similar alkyl-containing alkoxysilanes; vinyltrimethoxysilane, allyltrimethoxysilane, or similar alkenyl-containing alkoxysilanes; 3-glycidoxypropyl(methyl) dimethoxysilane, 3-glycidoxypropyl(methyl) diethoxysilane, 3-glycidoxypropyl(methyl) dibutoxysilane, 2-(3,4-epoxycyclohexyl)ethyl(methyl) dimethoxysilane, 2-(3,4-epoxycyclohexyl)ethyl(phenyl) diethoxysilane, 2,3-epoxypropyl(methyl) dimethoxysilane, 2,3-epoxypropyl (phenyl) dimethoxysilane, 3-glycidoxypropyl trimethoxysilane, 3-glycidoxypropyl triethoxysilane, 3-glycidoxypropyl tributoxysilane, 2-(3,4-epoxycyclohexyl) ethyltrimethoxysilane, 2-(3,4-epoxycyclohexyl) ethyltriethoxysilane, 2,3-epoxypropyltrimethoxysilane, 2,3-epoxypropyltriethoxysilane, or similar epoxy-containing alkoxysilanes; 3-aminopropyl trimethoxysilane, N-(2-aminoethyl)-3-aminopropyl trimethoxysilane, 3-aminopropyl trimethoxysilane, N-phenyl-3-aminopropyl trimethoxysilane, or similar amino-containing alkoxysilanes; 3-methacryloxypropyl trimethoxysilane, or similar methacryloxy-containing alkoxysilanes.

The following description relates to a method used for preparation of the composite silicone rubber powder of the present invention.

The method of the invention consists of mixing components (A) and (B) and then adding and mixing component (C). Addition of component (C) to the composite silicone rubber powder obtained by premixing component (A) with component (B) improves dispersibility of the silicone rubber powder composed of component (A) the surface of which is coated with component (B). There are no special restrictions to equipment that can be used in the method of the invention for mixing the aforementioned components. For example, this may be a Henschel mixer or a super mixer.

In the method of the invention, component (B) should be added in an amount sufficient for coating the surface of component (A) and may depend on the content of the non-crosslinking oil in component (A). Normally, component (B) should be added in an amount of 0.1 to 100 parts by mass, preferably 1 to 50 parts by mass per 100 parts by mass of component (A). Regarding component (C), the latter should be added in an amount sufficient for imparting hydrophilic properties to the obtained composite silicone rubber powder. The amount of component (C) may also depend on the amount of component (B) added to component (A), but in general it should be within the range of 0.1 to 100 parts by mass, preferably 0.5 to 50 parts by mass per 100 parts by mass of component (A). If the amount of component (B) or (C) used for treating component (A) deviates from the recommended range, this will either impair flowability of the obtained composite silicone rubber powder or make it difficult to improve dispersity of the powder.

There are no special restrictions with regard to the temperature at which components are mixed. For example, they can be mixed at room temperature. Since component (A) has low flowability, and this property is adjusted by coating the surface of component (A) with component (B), duration of mixing should be determined by observing changes in the aforementioned property.

The following description relates to a coating material of the invention. A distinguishing feature of the coating material of the invention is that it comprises the aforementioned composite silicone rubber powder. This coating material may be of a room-temperature curable type, room-temperature drying type, or thermally curable type. It may be an aqueous type, oily type, or in a granulated form. It may be based on the use of a resin-type vehicle and formed as a polyurethane-resin coating material, butyral-resin coating material, long oil phthalic-acid resin coating material, alkyd-resin coating material, amino-alkyd-resin coating material comprising amino-resin and alkyd-resin, epoxy-resin coating material, acryl-resin coating material, phenol-resin coating material, silicone-modified epoxy-resin coating material, silicone-modified polyester- resin coating material, and silicone-resin coating material.

It is recommended that the aforementioned composite silicone rubber powder has affinity for or reactivity to the resin contained in this coating material. For example, for a coating material that utilizes an epoxy resin as a vehicle, it is recommended to use a composite silicone rubber powder that contains epoxy or amino groups, while for a coating material that utilizes a polyurethane or amino resin as a vehicle, it is recommended to use a composite silicone rubber powder having amino groups.

There are no special restrictions with regard to the amount in which the composite silicone rubber powder should be contained in the coating material. However, in order to obtain a uniform and soft coating material with good matting properties, it is recommended to use the aforementioned powder in an amount of 0.1 to 150 parts by mass, preferably 0.1 to 100 parts by mass, and even more preferably 0.1 to 50 parts by mass per 100 parts by mass of solid content in the coating material.

In addition to the composite silicone rubber powder, the coating material of the invention may contain methanol, ethanol, or a similar alcohol; methylethyl ketone, methylisobutyl ketone, or a similar ketone; ethyl acetate, butyl acetate, cellosolve acetate, or a similar ester; N,N-dimethylformamide, or a similar amide; hexane, heptane, octane, or a similar aliphtic hydrocarbon; toluene, xylene, or a similar aromatic hydrocarbon, or another organic solvent; pigment, thickener made from a high polymer compound, flame retarder, a weather-resistant agent, etc.

The following description relates to a cosmetic material of the invention. A distinguishing feature of the cosmetic material of the invention is that it comprises the aforementioned composite silicone rubber powder. Examples of such a cosmetic material is soap, body shampoo, face washing cream, or a similar cleansing cosmetic material; skin lotion, cream-emulsion, pack cosmetic, or a similar basic cosmetic; cosmetic powder, foundation, or a similar base makeup cosmetic material; lipstick, chick rouge, eye shadow, eye liner, mascara, or a similar eye cosmetic; manicure, or a similar makeup cosmetic; shampoo, hair rinse, hair dressing cosmetic, hair growth agent, hair restoring agent, hair dyeing agent, or a similar hair cosmetic; perfume, eau de cologne, or a similar aromatizing cosmetic; tooth paste; bath cosmetics; depilatory, shaving lotion, antiperspirant and deodorant, sun screen agent, or other special cosmetic substances. These cosmetics may be prepared in the form of aqueous solutions, oil solutions, emulsions, creams, foams, semi-solid substances, solid substances, or powders. If necessary, they can be prepared in the form of sprays.

The aforementioned cosmetic materials may contain the composite silicone rubber powder of the invention in an amount of 0.5 to 99.0 mass %, preferably 1.0 to 95 mass %. If the composite silicone rubber powder is contained in an amount exceeding the recommended upper limit, the effect of the cosmetic material will be lost. If, on the other hand, the added amount of the powder is below the recommended lower limit, it will be difficult to impart to the cosmetic material an improved feeling of use.

In addition to the composite silicone rubber powder of the invention, the cosmetic material may incorporate other cosmetic raw materials such as avocado oil, almond oil, olive oil, cacoa butter, sesame oil, wheat-embryo oil, safflower oil, shea butter, turtle oil, camelia oil, persic oil, castor oil, grape oil, macadamia nut oil, mink oil, egg yolk oil, Japanese wax, coconut oil, rose hip oil, hardened oil, or similar oils and fats; orange roughy oil, camauba wax, candelilla oil, whale wax, jojoba oil, mountain wax, beeswax, lanolin, or similar waxes; liquid paraffin, vaseline, paraffin, ceresin, microcrystalline wax, and squalane or other hydrocarbons; lauric acid, myristic acid, palmitic acid, stearic acid, oleic acid, behenic acid, undecylenic acid, oxystearic acid, linolic acid, lanolic acid, synthetic fatty acids, or other higher fatty acids; ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, or other alcohols; cholesterol, dihydrocholesterol, phytosterol, or other sterols; ethyl linolate, isopropyl myristate, isopropyl lanolin fatty acid esters, hexyl laurate, myristyl myristate, cetyl myristate, octyldecyl myristate, decyl oleate, octyldodecyl oleate, hexyldecyl dimethyloctanoate, cetyl isooctanoate, cetyl palmitate, glycerol trimyristate, glycerol tri(caprylcaproate), propylene glycol dioleate, glycerol triisostearate, glycerol tri(isooctanoate), cetyl lactate, myristyl lactate, diisostearyl malate, or other fatty acid esters; glycerol, propylene glycol, 1,3-butylene glycol, polyethylene glycol, sodium d,1-pyrrolidone carboxylate, sodium lactate, sorbitol, and sodium hyaluronate, or other moisturizers; higher fatty acid soaps, higher alcohol sulfuric acid esters, N-acyl glutamates, phosphoric acid esters, or other anionic surfactants; cationic surfactants; amphoteric surfactants such as betaine, amino acid, imidazoline, and lecithin type surfactants; nonionic surfactants such as polyhydric alcohol ester and ethylene oxide condensed type surfactants; colored pigments such as iron oxide; white pigments such as zinc oxide, titanium oxide, and zirconium oxide; body pigments such as mica, talc, and ceresite; silicone oils such as dimethylpolysiloxanes, methylphenylpolysiloxanes, octamethylcyclotetrasiloxane, decamethylcyclopentasiloxane, polyether-modified silicone oils, and amino-modified silicone oils; purified water; thickeners such as carrageenan, alginic acid, gum arabic, tragacanth gum, pectin, starch, xanthan gum, polyvinyl alcohols, polyvinylpyrrolidones, sodium polyacrylates, and polyethylene glycols; ultraviolet absorbing agents; antiflngal agents; antiinflammatory agents; antiperspirants; preservatives; fragrances; oxidation inhibitors; pH adjusting agents; and spray agents.

EXAMPLES

The composite silicone rubber powder of the invention, method of preparation thereof, as well as coating and cosmetic materials that contain the aforementioned powder will be further described in more detail with reference to practical and comparative examples. All characteristics shown in the examples were measured at 25° C. The characteristics of the silicone rubber powder and of the composite silicone rubber powder were measured by the methods described below.

[Flowability of (Composite) Silicone Rubber Powder]

This characteristic was evaluated by measuring amount left on seive (in mass %) when passing a silicone rubber powder or composite silicone rubber powder through a 100 mesh sieve (cell size 150 μm) of an air-jet sieve machine of Alpine Co., Ltd.

[Dispersibility of (Composite) Silicone Rubber Powder in Silicone Oil]

A silicone rubber powder or composite silicone rubber powder in an amount of 0.5 g was added to 20 ml of silicone oil (SH200 type, the product of Dow Corning Toray Silicone Co., Ltd., viscosity: 10 mPa·s). The mixture was poured into a 30 ml glass bottle, shaken ten times, and observed after standing still for 10 min. The following criteria were used for evaluation.]

○: Precipitated in the form of microparticles and was uniformly dispersed by shaking.

X: Precipitated as in ○ but in the form of larger particles; shaking caused floating of these particles.

The following method was used for evaluating properties of the coating materials.

[Appearance and Coefficient of Surface Reflection of a Coating Film Formed from Oil-Soluble Coating Material]

The coating material was prepared by mixing 2 parts by mass of composite silicone rubber powder for 20 sec. in a dental mixer with 10 parts by mass of a commercial long oil phthalic acid resin-type coating material (65 mass % of solid substance; the product of Kanpe Hapio Co., Ltd.; the material was applied with one stroke as an azure color house paint). This material was applied by a glass stick onto both sides of an aluminum plate (6 cm×15 cm), while the thickness of the applied material was controlled by attaching an adhesive tape to both sides of the aluminum plate. The coated plate was dried at room temperature in a draft for two days, whereby a coating film was formed. Reflectivity of the coating film was measured (according to JIS Z 8741) with the use of a glossimeter (micro-TRI-gloss-type, the product of BYK Gardner Co.) by varying the angle of incidence at 20°, 60°, and 85°.

The raw materials for the preparation of a composite silicone rubber powder used in practical and comparative examples are shown in Table 1.

TABLE 1

| Raw Material | Description |
| --- | --- |
| Silicone Rubber Powder | |
| A-1 | Silicone rubber powder obtained by curing an addition-curing-type silicone rubber composition that contains 2.8 mass % of a cyclic dimethylpolysiloxane of 20-mer to 30-mer with an average particle size of 4 μm and a hardness of 30 by type-A durometer according to JIS K 6253. |
| A-2 | Silicone rubber powder containing 3-glycidoxypropyl groups (epoxy equivalent = 5000) obtained by curing a condensation-curing-type silicone rubber composition that contains 3 mass % of a cyclic dimethylpolysiloxane of 20-mer to 30-mer and 3.5 mass % of a nonionic surfactant with an average particle size of 2 μm and a hardness of 30 by type-A durometer according to JIS K 6253. |
| A-3 | Silicone rubber powder obtained by curing an addition-curing-type silicone rubber composition that contains 50 mass % of a dimethylpolysiloxane having a viscosity of 100 mPa·s, with an average particle size of 4 μm and a hardness of 10 by type-A durometer according to JIS K 6253. |
| Inorganic Micro-Powder | |
| B-1 | Micro-powder of dry-process-type silica (Aerosil 200, the product of Nippon Aerosil Co., Ltd.) having an average size of primary particles within the range of 5 to 15 nm, BET specific surface area of 200 $m^2/g$, surface silanol group density of 4.2/100 $Å^2$. |
| Organic Silicon Compound | |
| C-1 | 3-glycidoxypropyl trimethoxysilane (SZ6040, the product of Dow Corning Toray Silicone Co., Ltd.) |
| C-2 | 3-methacryloxypropyl trimethoxysilane (SZ6030, the product of Dow Corning Toray Silicone Co., Ltd.) |
| C-3 | N-(2-aminoethyl)-3-aminopropyltrimethoxysilane (SH6020P, the product of Dow Corning Toray Silicone Co., Ltd.) |
| C-4 | 3-aminopropyltrimethoxysilane (AY43-059P, the product of Dow Corning Toray Silicone Co., Ltd.) |
| C-5 | Vinyltrimethoxysilane (SZ6300, the product of Dow Corning Toray Silicone Co., Ltd.) |
| C-6 | Methyltrimethoxysilane (SZ6070, the product of Dow Corning Toray Silicone Co., Ltd.) |

Practical Examples 1 to 6

Components in the mass ratios shown in Table 2 were added to a silicone rubber powder in a super mixer (Henschel-type mixer, V-20-type, 20-liter capacity, the product of Kawata Co., Ltd.) and were mixed for about 2 minutes at room temperature and with a rotation frequency of 2,000 rpm, whereby the components were crushed from their original lump condition. Following this, an inorganic micro-powder was added, and the components were mixed for another 3 min. at room temperature with a rotation frequency of 2000 rpm. After the composite silicone rubber powder acquired flowability, it was again combined with an organic silicon compound, and the components were again mixed at room temperature for 2 min. at 2,000 rpm. Characteristics of the obtained composite silicone rubber powder and characteristics of the oil-soluble coating were evaluated. The results of the evaluation are shown in Table 2.

Comparative Example 1

Characteristics of silicone rubber powder (A-1) and oil-soluble coating were evaluated. The results are shown in Table 2.

Comparative Example 2

A composite silicone rubber powder was obtained by the same method as in Practical Example 1, with the exception that organic silicon compound (C-1) was not used. Characteristics of the obtained silicone rubber powder and oil-soluble coating were evaluated. The results are shown in Table 2.

Comparative Example 3

Characteristics of silicone rubber powder (A-2) and oil-soluble coating were evaluated. The results are shown in Table 2.

Comparative Example 4

Components in the mass ratios shown in Table 2 were added to a silicone rubber powder (A-3) in a super mixer (Henschel-type mixer, V-20-type, 20-liter capacity, the product of Kawata Co., Ltd.) and were mixed for about 2 minutes at room temperature and with a rotation frequency of 2,000 rpm, whereby the components were crushed from their original lump condition. Following this, an inorganic micro-powder (B-1) was added, and the components were mixed for another 3 min. at room temperature with a rotation frequency of 2,000 rpm. After the composite silicone rubber powder acquired flowability, it was again combined with an organic silicon compound (C-4), and the components were again mixed at room temperature for 2 min. at 2,000 rpm.

Characteristics of the obtained composite silicone rubber powder and characteristics of the oil-soluble coating were evaluated. The results of the evaluation are shown in Table 2.

TABLE 2

| Characteristics | Practical Examples | | | | | | Comparative Examples | | | |
|---|---|---|---|---|---|---|---|---|---|---|
| | 1 | 2 | 3 | 4 | 5 | 6 | 1 | 2 | 3 | 4 |
| Components of Composite Silicone Rubber Powder (parts by mass) | | | | | | | | | | |
| Silicone Rubber Powder | | | | | | | | | | |
| (A-1) | 20 | 20 | 20 | 20 | 20 | — | 20 | 20 | — | — |
| (A-2) | — | — | — | — | — | 20 | — | — | 20 | — |
| (A-3) | — | — | — | — | — | — | — | — | — | 20 |
| Inorganic Silicon Compound | | | | | | | | | | |
| (B-1) | 3 | 3 | 3 | 3 | 3.4 | 3.4 | — | 3 | — | 4 |
| Organic Silicon Compound | | | | | | | | | | |
| (C-1) | 2 | — | — | — | — | — | — | — | — | — |
| (C-2) | — | 2 | — | — | — | — | — | — | — | — |
| (C-3) | — | — | 2 | — | — | — | — | — | — | — |
| (C-4) | — | — | — | — | — | 3 | — | — | — | 3 |
| (C-5) | — | — | — | 2 | — | — | — | — | — | — |
| (C-6) | — | — | — | — | 2 | — | — | — | — | — |
| Characteristics of Composite Silicone Rubber Powder | | | | | | | | | | |
| Flowability (pass %) | 99 | 99 | 99 | 99 | 99 | 99 | 52 | 99 | 90 | 42 |
| Dispersibility in Silicone Oil | ○ | ○ | ○ | ○ | ○ | ○ | X | ○ | X | X |
| Appearance of Coating Film Made of Oil Coating Material | Uniform, soft, non-glossy | | | | | | Non-uniform, rough, non-glossy | Glossy | Uniform soft, non-glossy | Non-uniform, rough, non-glossy |
| Matting properties (%) of Oil Coating Material | | | | | | | | | | |
| 20° | 0 | 1 | 2 | 1 | 0 | 0 | 55 | 1 | 2 | 35 |
| 60° | 3 | 4 | 8 | 3 | 3 | 2 | 77 | 13 | 20 | 45 |
| 85° | 30 | 24 | 27 | 26 | 24 | 19 | 83 | 49 | 53 | 55 |

Comparative Example 5

An emulsion was prepared in an emulsifier from 100 parts by mass of dimethylpolysiloxane capped at both molecular terminals with silanol groups (viscosity: 70 mPa·s), 10 parts by mass of 3-aminopropylmethoxysilane, 4 parts by mass of an nonionic surfactant (Nonipol 95, the product of Nippon Oils & Fats Co., Ltd.) and 50 parts by mass of water. Following this, a suspension was prepared of a silicone rubber powder having an average particle size of 2 gm and a type-A durometer hardness of 3 according to JIS K 6253. The obtained suspension in an amount of 100 parts by mass was mixed with 50 parts by mass of a silica sol (Snowtex 20L-type, product of Nissan Chemical Industry Co., Ltd.; 40 to 50 μm particle size; silica content: 20 mass %) and then additionally mixed with 3 parts by mass of 3-methacryloxypropyl trimethoxysilane. The obtained slurry was dried in a small type spray drier (Ashizawa-Niro Co., Ltd.) to obtain a composite silicone rubber powder with a 12 μm average particle size. Characteristics of the obtained composite silicone rubber powder and oil coating material were evaluated, and the results of the evaluation are shown in Table 3.

TABLE 3

| Characteristic | Example No. Comparative Example 5 |
|---|---|
| Characteristics of Composite Silicone Rubber Powder | |
| Flowability (pass %) | 46 |
| Dispersity in Silicone Oil | ○ |
| Appearance of Coating Film Made of Oil Coating Material | Non-uniform, rough, non-glossy |
| Matting Properties (%) of Oil Coating Material | |
| 20° | 35 |
| 60° | 52 |
| 85° | 71 |

Practical Example 7

A uniform mixture was prepared in a Henschel mixer by mixing 25 mass % of the composite silicone rubber powder obtained in Practical Example 6, 15 mass % of sericite surface-coated with dimethylpolysiloxane, 14 mass % of talc surface coated with dimethylpolysiloxane, 30 mass % of mica surface coated with dimethylpolysiloxane, 1.0 mass % of red iron oxide, 2.5 mass % of yellow iron oxide, and 0.2 mass % of black iron oxide. The obtained mixture was again uniformly mixed with a preliminarily prepared hot mixture of 10 mass % of dimethylpolysiloxane having 6 mPa·s viscosity and 2 mass % of beeswax, as well as with 0.2 mass % of a preservative and 0.1 mass % of a fragrance that were added dropwise. The product was subjected to press forming and prepared as a powder foundation. The obtained powder foundation was applied onto the faces of panelists who were selected to make functional evaluation of the product. The results are shown in Table 4.

[Functional Evaluation of Powder Foundation]

Functional evaluation of feeling of use or similar properties of the powder foundation was carried out by 10 panelists. Symbol (○) corresponds to the case when the product is approved by 8 or more panelists; symbol (Δ) corresponds to approval by 4 to 7 panelists; and symbol (X) corresponds to approval by 4 or fewer panelists.

Comparative Example 6

A powder foundation was prepared by the same method as in Practical Example 7, with the exception that silicone rubber powder (A-2) was used instead of the composite silicone rubber powder of Practical Example 6. Functional evaluation of the powder foundation was carried out in the same way as in Practical Example 7. The results are shown in Table 4.

TABLE 4

| Characteristics | Example No. | |
|---|---|---|
| | Practical Example 7 | Comparative Example 6 |
| Spreadability | ○ | Δ |
| Pasting | ○ | ○ |
| Feeling of Use | ○ | Δ |
| | Smooth, Dry touch | Feel of some roughness |
| Color uniformity | ○ | Δ |

INDUSTRIAL APPLICABILITY

Since the composite silicone rubber powder of the present invention possesses excellent dispersibility in coating and cosmetic materials, it can be used as an additive to thermosetting resin compositions, thermoplastic resin compositions, or as a surface lubricant to plastic films. When the aforementioned powder is compounded with coating materials, it can be used for the formation of coating films with matting properties and for improving appearance of plastic and metal products. When the composite silicone rubber powder of the invention is compounded with cosmetic materials, it improves their feeling of use and therefore can be used in conjunction with skin and make-up cosmetics.

The invention claimed is:

1. A composite silicone rubber powder comprising: (A) a silicone rubber powder having an average particle size within the range of 0.1 to 500 μm and hardness of at least 15 by type A durometer according to JIS K 6253, wherein the surface of said silicone rubber powder is coated with (B) a microfine inorganic powder having the BET specific surface area of at least 10 m²/g, said composite silicone rubber powder being characterized by the fact that the surface thereof is treated with (C) an organic silicon compound having a silicon-bonded hydrolyzable group, or with a product of partial hydrolysis of said organic silicon compound.

2. The composite silicone rubber powder of claim 1, wherein said component (B) is a microfine metal oxide powder.

3. The composite silicone rubber powder of claim 1, wherein said component (B) is a microfine silica powder.

4. The composite silicone rubber powder of claim 1, wherein said hydrolyzable group of component (C) is an alkoxy group.

5. The composite silicone rubber powder of claim 1, wherein said component (A) has an average particle size within the range of 0.1 to 100 μm.

6. The composite silicone rubber powder of claim 1, wherein said component (A) has a hardness of 15 to 80 by type A durometer according to JIS K 6253.

7. The composite silicone rubber powder of claim 1, wherein said component (A) is formed from a silicone rubber composition selected from the group of addition-reaction-curable silicone rubber compositions, condensation-reaction-curable silicone rubber compositions, and silicone rubber compositions curable with organic peroxide.

8. A method of manufacturing the composite silicone rubber powder of claim 1 comprising the steps of: mixing (A) a silicone rubber powder having an average particle size within the range of 0.1 to 500 μm and hardness of at least 15 by type A durometer according to JIS K 6253 with (B) a microfine inorganic powder having the BET specific surface area of at least 10 m²/g; and further mixing the obtained mixture with (C) an organic silicon compound having a silicon-bonded hydrolyzable group, or with a product of partial hydrolysis of said organic silicon compound.

9. The method of claim 8, wherein said component (B) is a microfine metal oxide powder.

10. The method of claim 8, wherein said component (B) is a microfine silica powder.

11. The method of claim 8, wherein said hydrolyzable group of component (C) is an alkoxy group.

12. The method of claim 8, wherein said component (A) has an average particle size within the range of 0.1 to 100 μm.

13. The method of claim 8, wherein said component (A) has a hardness of 15 to 80 by type A durometer according to JIS K 6253.

14. The method of claim 8, wherein said component (A) is formed from a silicone rubber composition selected from the group of addition-reaction-curable silicone rubber compositions, condensation-reaction-curable silicone rubber compositions, and silicone rubber compositions curable with organic peroxide.

15. A coating material containing the composite silicone rubber powder according to claim 1.

16. A cosmetic material containing the composite silicone rubber powder according to claim 1.

17. A composite silicone rubber powder comprising: (A) a silicone rubber powder having an average particle size within the range of 0.1 to 500 μm and hardness of at least 15 by type A durometer according to JIS K 6253, wherein the surface of said silicone rubber powder is coated with (B) a microfine metal oxide powder having the BET specific surface area of at least 10 m²/g, said composite silicone rubber powder being characterized by the fact that the surface thereof is treated with (C) an organic silicon compound having a silicon-bonded alkoxy group, or with a product of partial hydrolysis of said organic silicon compound.

18. The composite silicone rubber powder of claim 17, wherein said component (A) has an average particle size within the range of 0.1 to 100 μm.

19. The composite silicone rubber powder of claim 17, wherein said component (A) has a hardness of 15 to 80 by type A durometer according to JIS K 6253.

20. The composite silicone rubber powder of claim 17, wherein said component (A) is formed from a silicone rubber composition selected from the group of addition-reaction-curable silicone rubber compositions, condensation-reaction-curable silicone rubber compositions, and silicone rubber compositions curable with organic peroxide.

* * * * *